United States Patent [19]

Goosen

[11] 4,018,228

[45] Apr. 19, 1977

[54] SURGICAL PUNCH APPARATUS

[76] Inventor: Carl C. Goosen, 1035 Golfside Drive, Winter Park, Fla. 32789

[22] Filed: Feb. 24, 1975

[21] Appl. No.: 552,703

[52] U.S. Cl. .............................. 128/305; 30/241; 83/690

[51] Int. Cl.² .................................. A61B 17/32

[58] Field of Search ............... 128/2 B, 305, 305.3; 30/241, 242; 83/690

[56] References Cited

UNITED STATES PATENTS

| 1,867,624 | 7/1932 | Hoffman | 128/305 X |
| 2,433,058 | 12/1947 | Mesaros | 83/690 X |
| 2,505,358 | 4/1950 | Gusberg et al. | 128/2 B |
| 2,994,321 | 8/1961 | Tischler | 128/2 B |
| 3,104,666 | 9/1963 | Hale et al. | 128/305.3 |
| 3,776,237 | 12/1973 | Hill et al. | 128/305 |
| 3,837,345 | 9/1974 | Matar | 128/305 |

FOREIGN PATENTS OR APPLICATIONS

H24,669  10/1956  Germany ................ 30/242

OTHER PUBLICATIONS

Catalog No. 107 B of E. &. J. Swigart Co., p. 75, Washington, D.C., 1968.

Primary Examiner—Channing L. Pace
Attorney, Agent, or Firm—Duckworth, Hobby, Orman, Allen & Pettis

[57] ABSTRACT

A surgical punch instrument having an elongated, hollow sleeve with an elongated rod sliding therein and extending through one end of the hollow sleeve. The elongated rod has a narrowed end portion and fixed cylindrical blade attached thereto while the open end of the hollow sleeve has a hollow, cylindrical blade removably attached thereto. The sliding rod may be actuated by a handle attached thereto and extending through the elongated sleeve to pull the blade on the end of the rod into the hollow blade in the hollow sleeve thereby shearing or punching an opening in tissue therebetween.

8 Claims, 7 Drawing Figures

U.S. Patent   April 19, 1977   Sheet 1 of 2   4,018,228
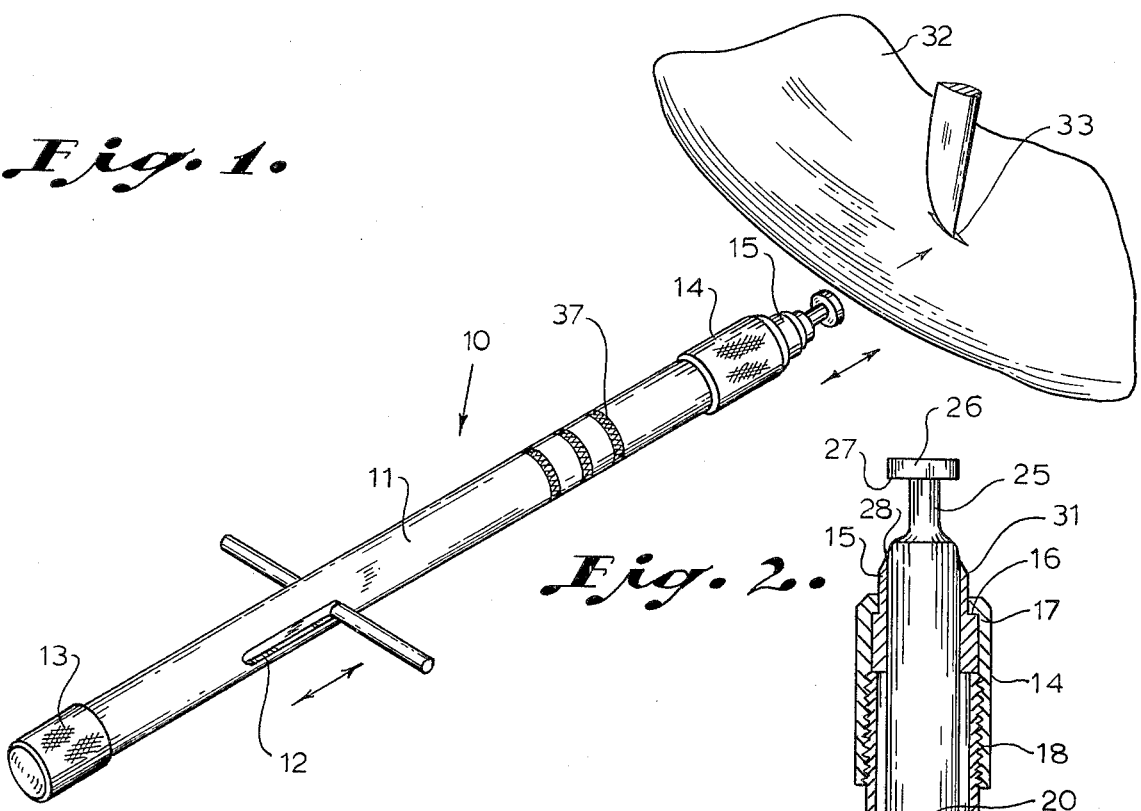
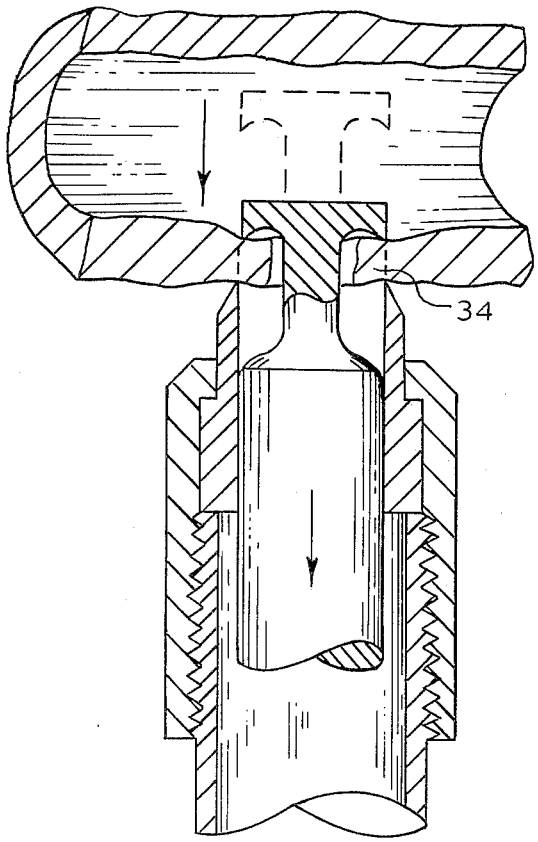
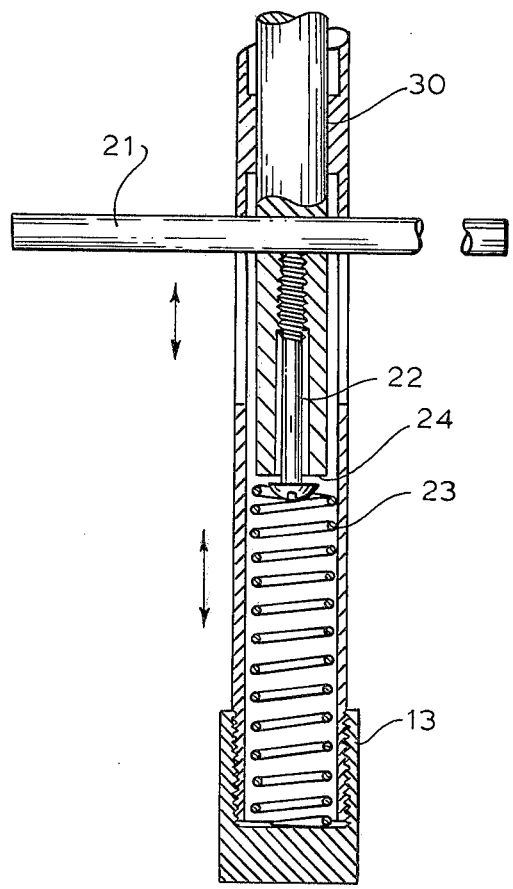

SURGICAL PUNCH APPARATUS

BACKGROUND OF THE INVENTION

The present invention relates to surgical instrument and more particularly to an aorta punch for use in saphenous vein grafts, and the like.

In cardiac surgery, saphenous vein grafts are used to bypass diseased areas of the coronary arteries, and the present invention is used in the preparation of an opening in the ascending aorta where the proximal end of the saphenous vein may be anastomosed. In the past, incisions in the aorta were made with surgical scalpels or scissors or combinations of these with the shape varying from widened slits to triangular. It has also been suggested to use various punches in an attempt to provide an accurate, clean circular opening. The function of such a punch depends on the introduction of a support, or anvil into the aorta or artery through an incision in the arterial wall. Using one hand, the thumb and opposed first and second fingers are approximated to pull a cross-bar which pulls down a tubular cutting device which pushes the aortic wall against an anvil in the lumen. Great pressure has to be exerted in order to accomplish the desired result. Such a system has proved unsatisfactory because of the great pressure required by a blade pushing against an anvil. Accordingly, it is one purpose of the present invention to overcome the disadvantages mentioned and to provide a cutting mechanism with a shearing, or scissor-like action. This is accomplished by allowing the portion of the shearing punch which is introduced into the vessel lumen to share in the cutting action as a fixed blade which slides into the cutting blade to "punch" an opening. Pressure is maintained on the instrument until the "plug" has been removed in order to avoid leaving any residue in the aorta which could constitute an embolus. The side of the fixed blade which opposes the circular cutter is hollow ground to facilitate the cutting action. To achieve an ideal opening, especially since the presence of adventitia in the area readily binds the cutting mechanism, demands a razor-like cutting edge and a very close tolerance between the two shearing edges, the instrument has to be manufactured as a precision instrument with disposable cutting blades.

SUMMARY OF THE INVENTION

The present invention relates to surgical instruments and especially to a surgical punch for use in cardiac surgery in saphenous vein grafts which are used to bypass diseased areas of the coronary arteries. An elongated, hollow support sleeve has an elongated rod slidably mounted therein which may extend out an open end of said hollow support sleeve. A fixed cutter blade is removably attached to one end of the support sleeve with the elongated rod passing therethrough and having a movable cutter blade fixedly attached to the end thereof. The movable cutter blade has diameter smaller than the removable cutting blade whereby it can be pulled thereinto to give a shearing, cutting action. The handle is attached to the sliding rod and passes through slots in the elongated, hollow support sleeve whereby the handle can actuate the rod to pull the removable cutter blade into the fixed cutter blade to cut a predetermined shaped opening in tissue. The blades may be specially shaped and the rod may be spring loaded and the entire apparatus provides for ease in disassembly, cleaning and disinfecting for re-use.

BRIEF DESCRIPTION OF THE DRAWING

Other objects, features and advantages of this invention will be apparent from the written description and the drawings in which:

FIG. 1 is a perspsective view of an aorta punch in accordance with the present invention shown in connection with a cardiac section;

FIG. 2 is a sectional view of the embodiment of FIG. 1;

FIG. 3 is a sectional view of the cutting blades and cardiac section showing the operation of the blades;

DESCRIPTION OF THE PREFERRED EMBODIMENTS

Figure 4:
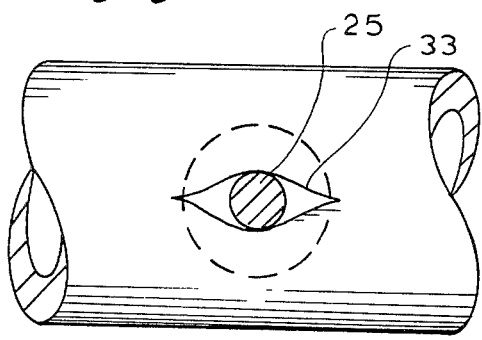
FIG. 4 is a sectional view of the fixed blade extending into a vein and having an enlarged rod section for producing an oval opening.

Referring now to the drawings and especially to FIGS. 1 through 3, a preferred embodiment of the present invention 10 is illustrated having an elongated, cylindrical tube or sleeve 11, with a pair of slots 12 cut therein along with a knurled and threaded cap 13 at one end and a knurled and threaded blade locking cap 14 at the other end for holding a cylindrical, hollow blade 15 onto the end of the sleeve 11. Blade 15 has an annular ledge 16 surrounding the blade 15 which is held by an internal annular ledge 17 in the locking member 14 which is threaded with threads 18 to the sleeve 11. An internal sliding rod 20 is located inside of the sleeve 11 and has a handle 21 passing therethrough and through slots 12 of the sleeve 11. Handle 21 is attached to rod 20 by means of a threaded screw 22 and is spring biased towards the blade end by a spring 23 held in place by the end cap 13 and pushes against the blunt end 24 of rod 20. Rod 20 has a narrowed portion 25 formed in one end thereof which holds a movable fixedly attached blade 26 having a cutting edge 27. Blade 26 is of a slightly smaller diameter than blade 15 so that blade 26 which is generally disc-shaped will slide inside the hollow blade 15 with a close fit to perform a shearing action between the blade 15 and 26. Cutting edge 27 of blade 26 works in connection with the cutting edge 28 of the blade 15 which has been angled inwardly and may be hollow ground to provide a sharp cutting action between the blades as the blade 26 is slid into the blade 15. Blade 26 is actuated by pulling the handle 21 which slides the rod 20 which rides on a raised, annular portion 30 located inside the sleeve 11 and also rides on the internal surface 31 of the blade 15.

The surgical instrument in accordance with FIG. 1 through 3 is designed primarily for use in implanting a coronary graft such as an aorta coronary bypass which is accomplished by the grafting of saphenous vein between the ascending aorta 32 by a small cut 33 with the other end of the saphenous vein attached to a coronary artery. The disc-shaped movable blade 26 is inserted through the cut 33 as illustrated in FIG. 3 with the narrowed portion 25 passing therethrough. Pulling of the handle 21 to slide the rod 20 in the sleeve 11 pulls the blade 26 to shear a circular plug 34 from the aorta wall by the cutting action of the blades 26 and 15. The saphenous vein may then be attached over the opening created by the removal of the punched hole.

Figure 5:
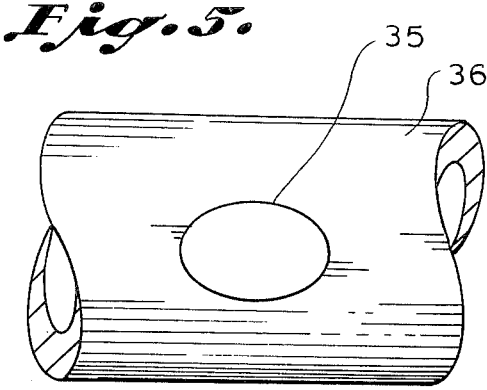
FIG. 5 is an oval opening in accordance with the cut made in FIG. 4.

FIGS. 4 and 5 illustrate that by enlarging the diameter of the narrowed portion 25 so as to further spread the small slit 33 during the punching operation will produce an oval opening 35 in the vein 36. An oval opening more naturally approximates the opening where branches of vessels take off which is usually not at right angles. Therefore, the elliptical opening may find favor with some surgeons.

The present invention would typically be made of high quality surgical stainless steel and may be easily disassembled for cleaning and disinfection by removing the caps 13 and 14 and loosening the screw 22 for removing the handle 21 thereby allowing all of the parts to slip free from each other. Advantageously, the blade 15 can be quickly replaced by removing the knurled locking cap 14, and sliding a new blade in place. Blade 15 is required to be maintained very sharp in order to cleanly cut the opening desired. The apparatus may also be produced in various sizes to match differences in vein graft diameters. Typically, three sizes would be satisfactory which can be identified by rings 37 of FIG. 1 the one ring or two rings or three rings identifying the three differenct sizes.

Figure 6:
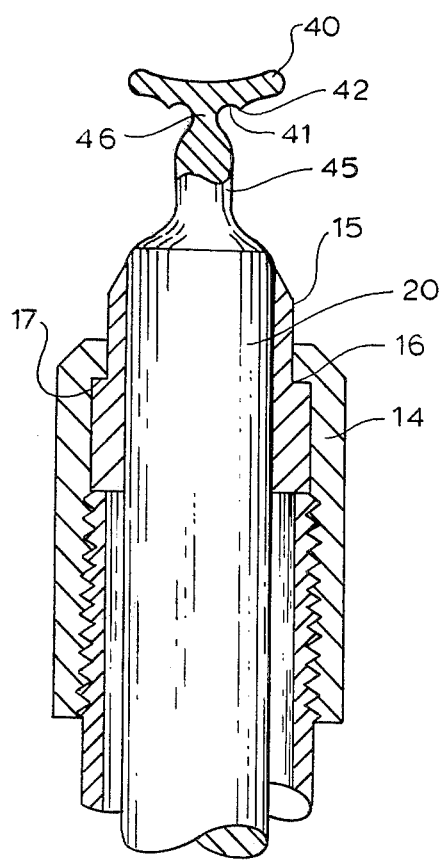
FIG. 6 is a sectional view of a second embodiment for eye surgery.
Figure 7:
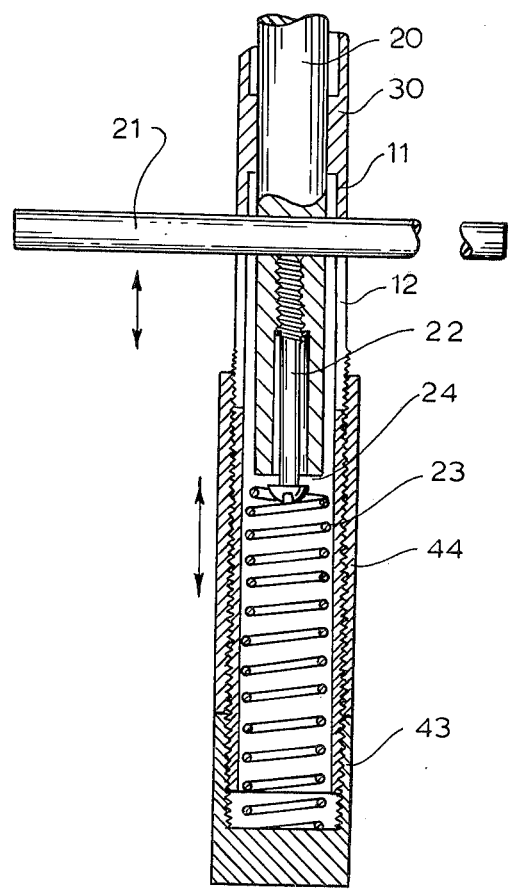
FIG. 7 is a sectional view of the embodiment of FIG. 6.

Referring now to FIGS. 6 and 7, an extension of the basic shearing punch may be applied to the field of eye surgery as relates to cornea transplants. At present, trephines are used for shaping the cornea of the donor eye for transplant. Trephines of identical size are used to remove the cornea from the patient. The trephine blade is adjusted to penetrate the cornea to 75% of its thickness in order that vital, irreplaceable fluid is not lost from the antechamber of the eye. A complete removal of the cornea is then carried out with blades and scissors. It is not necessary to protect the endothelium of that portion of the cornea which is removed from the patient and since a simple clean cut single shearing action removes the diseased cornea, the shearing punch has been modified to handle this operation. The overall length of the instrument has been reduced to conform to standards required for surgery under the binocular microscope as illustrated in FIG. 7 and the fixed blade 40 has been reduced in thickness and hollowed on the side facing the lens of the eye at 41. The hollow ground aspect has been polished and the sharp ridge 42 has been placed near the stem carrying the fixed blade to aid and prevent lateral slip so that more accurate removal of the cornea is possible and an adjustable ring has been placed around the sleeve 11 which limits the movement of the rod 20 so that the moving blade does not penetrate the antechamber too deeply. The sleeve has a cap 43 with a locking ring 44 threaded thereto and holding the spring 23 against the blunt end 24 of the rod 20 and the threaded screw 22 holds the handle 21 in place passing through slots 12 of the sleeve 11. The raised portion 30 is maintained in the sleeve 11 as is the removable annular cutting blade 15 held by locking cap 14 abutting their respective ledges 16 and 17. A narrowing portion 45 of the rod 20 carrying the fixed blade 40 has a further narrowing or waist 46 so that the unit may be attached by sutures to the cornea to insure centering before excision.

It should be clear to those skilled in the art that a surgical instrument improving the punching of an aorta wall for a coronary bypass has been provided but it should also be clear that the present invention can be utilized in the field of eye surgery in cornea transplants without departing from the spirit and scope of the invention. Accordingly, the present invention is not to be construed as limited to the particular forms disclosed herein since these are to be regarded as illustrative rather than restrictive.

I claim:
1. A surgical punch apparatus comprising in combination:
   an elongated hollow support sleeve having two end portions;
   a removably attached annular cutter blade attached to one end portion of said elongated hollow support sleeve and having an axial passage therethrough;
   an elongated rod slidably mounted in said hollow support sleeve;
   a movable cutter blade fixedly attached to one end of said elongated rod and slidable with said rod in said sleeve, said movable cutter blade being disc-shaped with an annular cutting edge and shaped to slide into the passage in said removably attached cutter blade;
   handle means attached to said elongated rod and extending through openings in said elongated hollow support sleeve for sliding said rod;
   threaded blade holding member on the end of said elongated hollow support sleeve for holding said removably attached cutter blade to said elongated hollow support sleeve;
   said removably attached cutter blade having an annular ledge wrapped around the exterior thereof and said threaded blade holding member having an interior annular ledge therein whereby the interior ledge of the threaded blade holding member will abut against the annular ledge of the blade for holding the blade to the hollow support sleeve;
   said elongated hollow support sleeve having a raised annular portion therein having substantially the same interior cross-section diameter as said removably attached cutter blade and said elongated rod being slidably supported on said raised annular portion and said removably attached cutter blade; and
   a cap attached to the opposite end of said elongated hollow support sleeve from said threaded blade holding member and a spring located between said cap and said elongated rod in said elongated hollow support sleeve, whereby said fixed cutter blade can be inserted in a cut and pulled into said removably attached cutter blade to a cut a predetermined section in tissue.

2. The apparatus in accordance with claim 1 in which said elongated rod has a narrowed portion in one end portion thereof connecting the remainder of said rod to said movable cutter blade fixedly attached thereto.

3. The apparatus in accordance with claim 1 in which said removably attached cutter blade is a hollow, cylindrical shape with an interior cross-section diameter slightly larger than said movable disc-shaped cutter blade.

4. The apparatus in accordance with claim 1 in which said removably attached cutter blade has hollow ground cutting edge angled towards the center of said blade.

5. The apparatus in accordance with claim 1 in which said handle means is held to said elongated rod with a threaded member and may be disengaged and removed.

6. The apparatus in accordance with claim 1 in which said elongated, hollow support sleeve has annular markings to indicate the apparatus size.

7. The apparatus in accordance with claim 1 in which said movable cutter blade is a carved disc and has an annular cutting edge between the perimeter of said cutting blade and its center axis.

8. The apparatus in accordance with claim 7 in which said narrowed portion of said rod has a second narrowed portion between said first narrowed portion and said movable cutter blade.

* * * * *